United States Patent
Parihar et al.

(10) Patent No.: US 8,409,217 B2
(45) Date of Patent: Apr. 2, 2013

(54) TISSUE RETRIEVAL DEVICE WITH BLADDERS

(75) Inventors: Shailendra K. Parihar, Mason, OH (US); Atul M. Godbole, Liberty Township, OH (US); Kevin A. Larson, South Lebanon, OH (US); Gregory W. Johnson, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 386 days.

(21) Appl. No.: 12/692,733

(22) Filed: Jan. 25, 2010

(65) Prior Publication Data
US 2011/0184432 A1    Jul. 28, 2011

(51) Int. Cl.
*A61B 17/22* (2006.01)
(52) U.S. Cl. .................................. 606/127
(58) Field of Classification Search .......... 606/110, 606/113, 114, 115, 127, 128; 600/184
See application file for complete search history.

(56) References Cited

U.S. PATENT DOCUMENTS

| | | | |
|---|---|---|---|
| 5,190,555 A | 3/1993 | Wetter et al. | |
| 5,215,521 A | 6/1993 | Cochran et al. | |
| 5,320,627 A | 6/1994 | Sorensen et al. | |
| 5,337,754 A * | 8/1994 | Heaven et al. | 600/562 |
| 5,370,647 A | 12/1994 | Graber et al. | |
| 5,465,731 A | 11/1995 | Bell et al. | |
| 5,480,404 A | 1/1996 | Kammerer et al. | |
| 5,524,633 A * | 6/1996 | Heaven et al. | 600/562 |
| 5,647,372 A | 7/1997 | Tovey et al. | |
| 5,649,902 A | 7/1997 | Yoon | |
| 5,735,289 A | 4/1998 | Pfeffer et al. | |
| 5,769,794 A | 6/1998 | Conlan et al. | |
| 5,779,716 A | 7/1998 | Cano et al. | |
| 5,836,953 A | 11/1998 | Yoon | |
| 5,971,995 A | 10/1999 | Rousseau | |
| 6,409,733 B1 | 6/2002 | Conlon et al. | |

(Continued)

FOREIGN PATENT DOCUMENTS

| | | |
|---|---|---|
| DE | 92 18 154 | 9/1993 |
| DE | 10 2008 019497 | 10/2009 |

(Continued)

OTHER PUBLICATIONS

International Search Report and Written Opinion dated Aug. 1, 2011 for Application No. PCT/US2011/021042.

(Continued)

*Primary Examiner* — Ryan Severson
*Assistant Examiner* — Jonathan W Miles
(74) *Attorney, Agent, or Firm* — Frost Brown Todd LLC

(57) ABSTRACT

A tissue retrieval device includes an introducer tube and a tissue retrieval bag. The introducer tube is sized to be inserted into a patient through a trocar. The tissue retrieval bag may be selectively exposed at the distal end of the introducer tube within the patient. The tissue retrieval bag may receive a tissue specimen and be withdrawn from the patient. The tissue retrieval bag may include an inflatable portion. When inflated, the inflatable portion may extend the tissue retrieval bag from a contracted configuration to an expanded configuration. The inflatable portion may substantially seal a tissue specimen within the tissue retrieval bag. The tissue retrieval bag may me formed of an environmentally sensitive material such that the size of the tissue retrieval bag expands when the tissue retrieval bag is exposed within the patient.

19 Claims, 13 Drawing Sheets

U.S. PATENT DOCUMENTS

| | | |
|---|---|---|
| 6,673,080 B2 | 1/2004 | Reynolds et al. |
| 7,691,111 B2 | 4/2010 | Bates et al. |
| 7,762,959 B2 | 7/2010 | Bilsbury |
| 8,016,771 B2 | 9/2011 | Orban, III |
| 2004/0138587 A1 | 7/2004 | Lyons |
| 2005/0267492 A1 | 12/2005 | Poncet et al. |
| 2006/0200170 A1 | 9/2006 | Aranyi |
| 2006/0247663 A1 | 11/2006 | Schwartz et al. |
| 2007/0088370 A1 | 4/2007 | Kahle et al. |
| 2011/0184311 A1 | 7/2011 | Parihar et al. |
| 2011/0184430 A1 | 7/2011 | Parihar et al. |
| 2011/0184431 A1 | 7/2011 | Parihar et al. |
| 2011/0184432 A1 | 7/2011 | Parihar et al. |
| 2011/0184433 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |

FOREIGN PATENT DOCUMENTS

| | | |
|---|---|---|
| EP | 0 578 997 | 1/1994 |
| EP | 0 950 376 | 10/1999 |
| WO | WO 93/15671 | 8/1993 |
| WO | WO 95/09666 | 4/1995 |
| WO | WO 98/38920 | 9/1998 |
| WO | WO 01/10308 | 2/2001 |
| WO | WO 2005/112783 | 12/2005 |

OTHER PUBLICATIONS

International Search Report dated Apr. 4, 2011 for Application No. PCT/US2011/021817.

International Search Report dated Apr. 19, 2011 for Application No. PCT/US2011/021046.

International Search Report dated Oct. 11, 2011 for Application No. PCT/US2011/021049.

\* cited by examiner

TISSUE RETRIEVAL DEVICE WITH BLADDERS

BACKGROUND

Endoscopic surgery (e.g., laparoscopy) is a procedure wherein surgery is performed through a series of small openings or incisions in a patient. This type of surgery may reduce or eliminate the need for large incisions and may change some otherwise open surgical procedures such as gall bladder removal to simple outpatient surgery. Consequently, the patient's recovery time may change from weeks to days. These types of surgeries may be used for repairing defects or for the removal of diseased tissue or organs from areas of the body such as the abdominal cavity. In some of these procedures, biological material or tissue may be removed or excised from the body through a small opening such as an incision, a small natural orifice, or through a small diameter laparoscopic access port such as a trocar.

Various types of tissue retrieval pouches or bags have been developed to allow for the removal of tissue through a small opening, orifice, or port in an endoscopic surgical procedure. Various instruments have also been devised for introducing, opening, positioning, and closing tissue retrieval bags within a patient; and for removing the bags and enclosed tissue from the surgical site. Some exemplary retrieval bags and associated instruments are disclosed in U.S. Pat. No. 5,465,731, entitled "Specimen Retrieval Pouch and Method for Use," issued Nov. 14, 1995, the disclosure of which is incorporated by reference herein; U.S. Pat. No. 5,480,404, entitled "Surgical Tissue Retrieval Instrument," issued Jan. 2, 1996, the disclosure of which is incorporated by reference herein; U.S. Pat. No. 5,647,372, entitled "Specimen Retrieval Pouch and Method for Use," issued Jul. 15, 1997, the disclosure of which is incorporated by reference herein; U.S. Pat. No. 5,971,995, entitled "Surgical Pouch Instrument," issued Oct. 26, 1999, the disclosure of which is incorporated by reference herein; and U.S. Pat. No. 6,409,733, entitled "Specimen Retrieval Bag," issued Jun. 25, 2002, the disclosure of which is incorporated by reference herein.

While a variety of tissue retrieval devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

Figure 1:
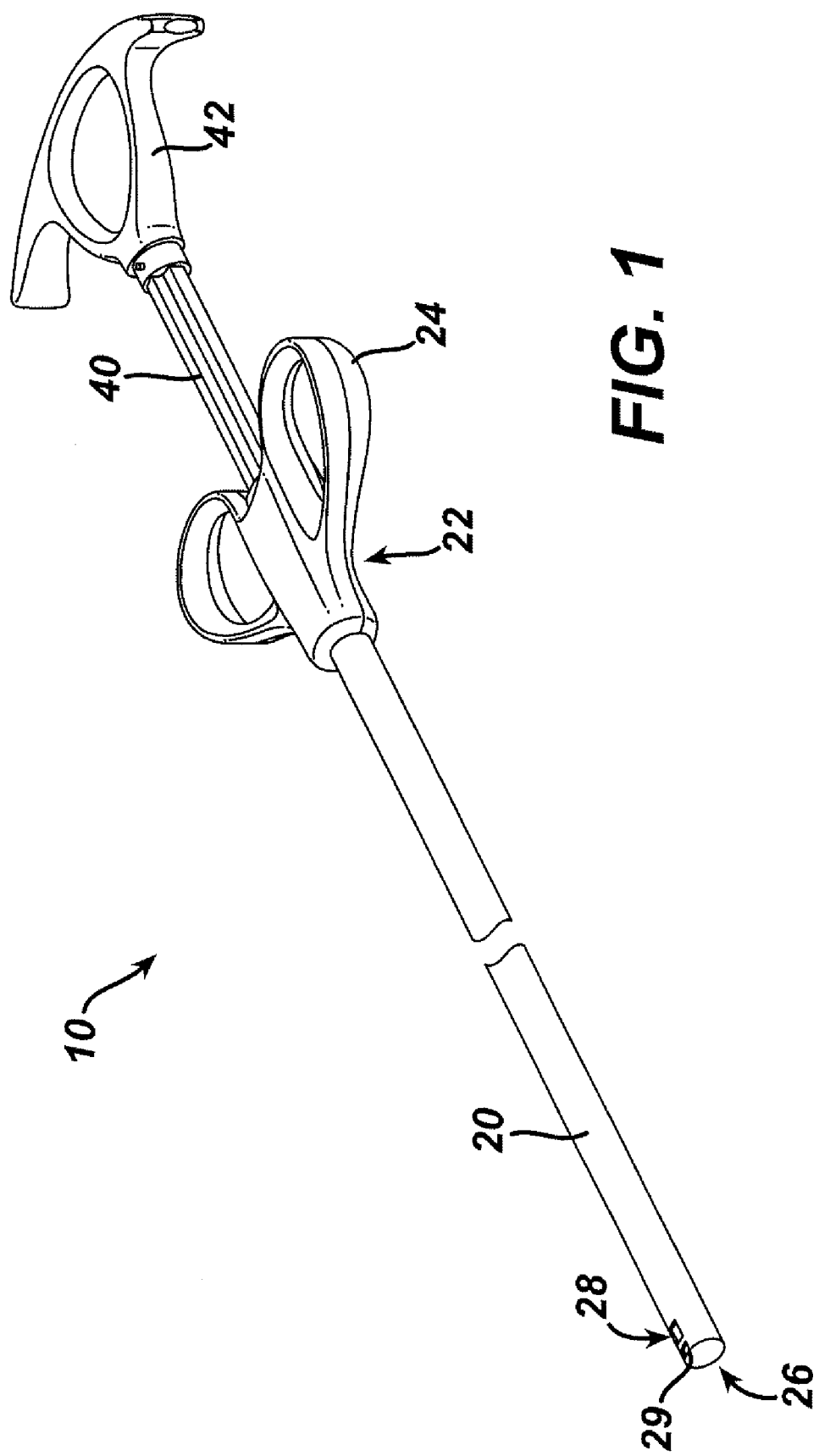
FIG. 1 is a perspective view of an exemplary tissue retrieval device, with a retrieval bag in a retracted position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

Figure 2:
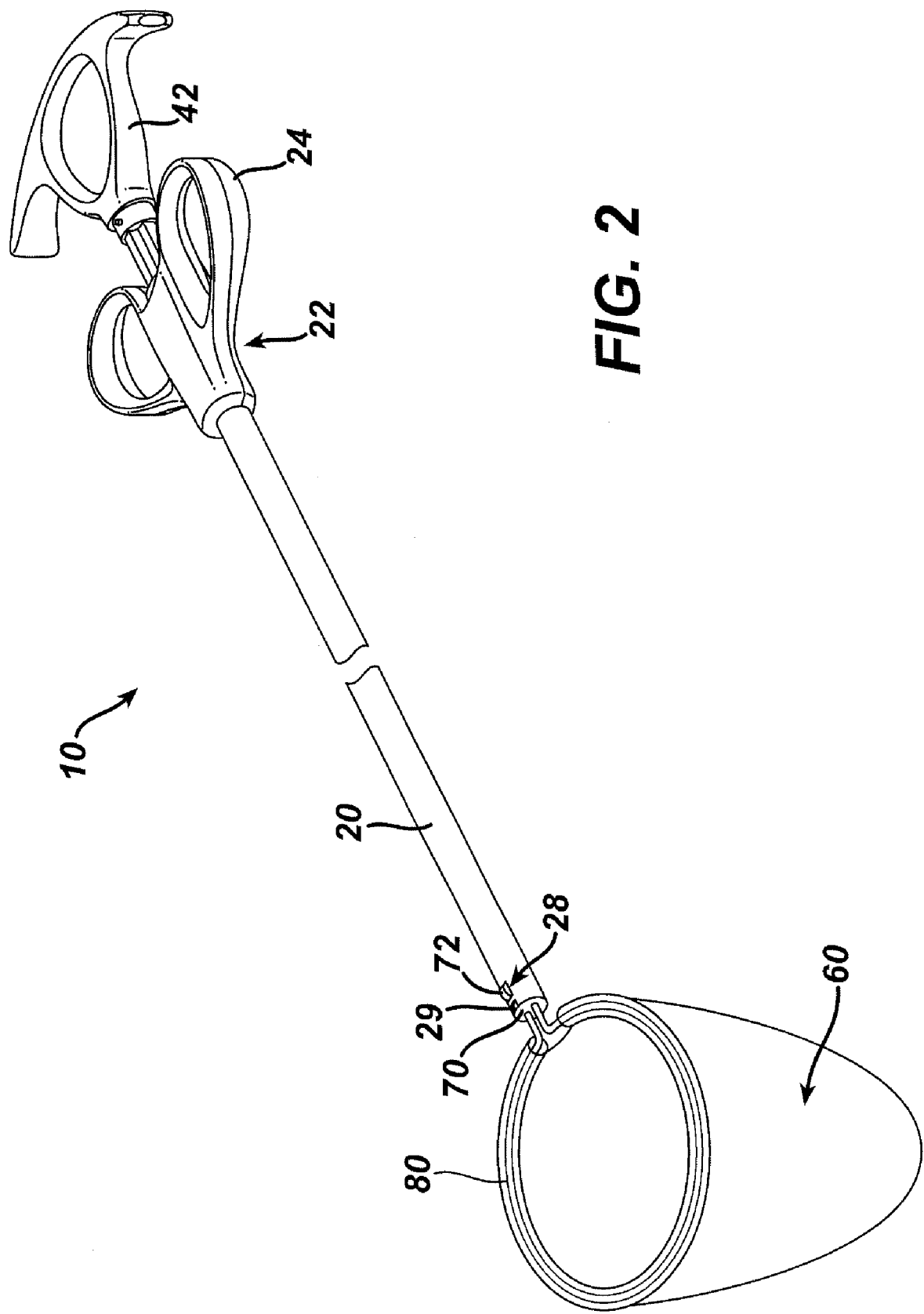
FIG. 2 is a perspective view of the tissue retrieval device of FIG. 1, with the retrieval bag in a deployed position.
Figure 3:
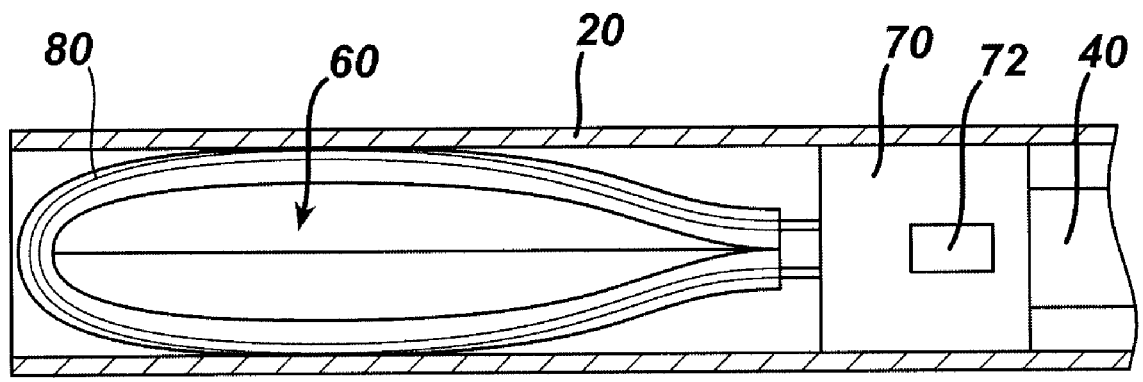
FIG. 3 is a partial top view of the tissue retrieval device of FIG. 1, with the retrieval bag in the retracted position and with the introducer tube shown in cross section.
Figure 4:
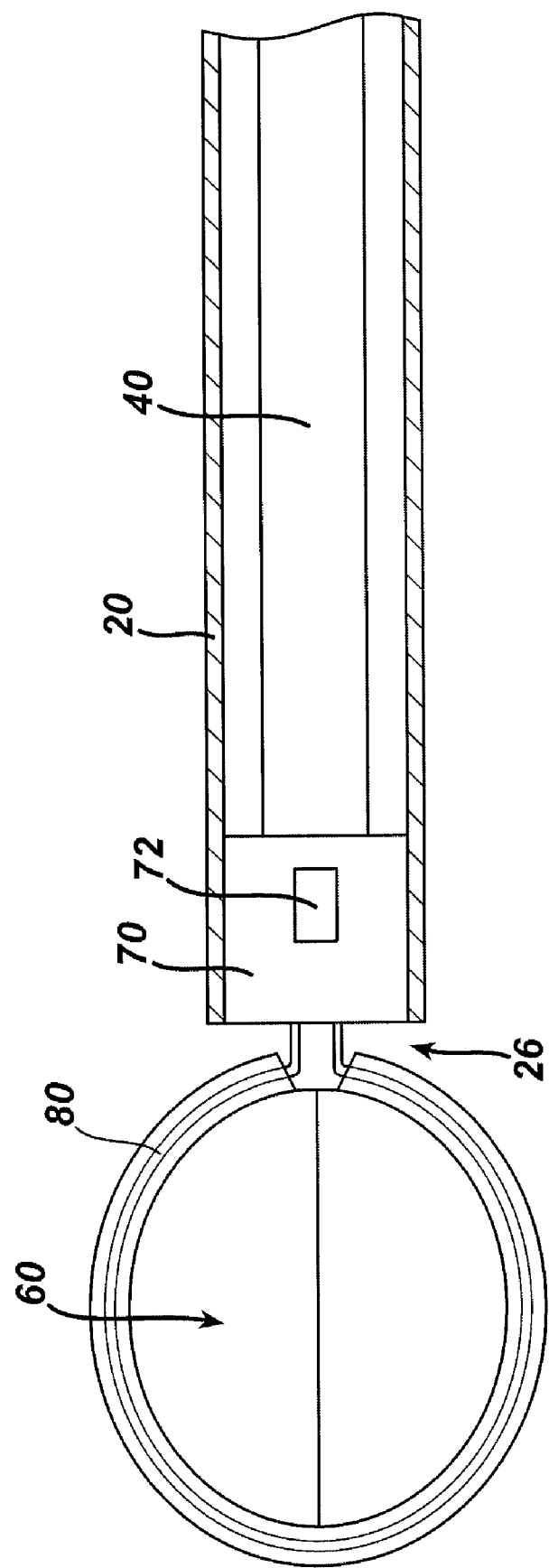
FIG. 4 is a partial top view of the tissue retrieval device of FIG. 1, with the retrieval bag in the deployed position and with the introducer tube shown in cross section.

FIGS. 1-4 show an exemplary tissue retrieval device (10). In this example, tissue retrieval device (10) comprises an elongate introducer tube (20), a handle (22) secured to the proximal end of introducer tube (20), an actuating rod (40), and a thumb ring (42) secured to the proximal end of actuating rod (40). Handle (22) comprises a pair of finger grips (24). As will be described in greater detail below, actuating rod (40) is slidable within the hollow interior of introducer tube (20) to selectively deploy a tissue retrieval bag (60) from introducer tube (20). In particular, with actuating rod (40) in a proximal position as shown in FIGS. 1 and 3, a user may insert their thumb in thumb ring (42), and insert their index and middle fingers in finger grips (24), then advance thumb ring (42) distally toward finger grips (24) to translate actuating rod (40) distally to a distal position as shown in FIGS. 2 and 4.

In the present example introducer tube (20) is formed of metal; while handle (22), actuating rod (40), and thumb ring (42) are formed of plastic. However, it should be understood that any suitable material or combination of materials may be used to form these components and other components described herein. Introducer tube (20) has an open distal end (26) and a side aperture (28) just proximal to open distal end (26). Introducer tube (20) of the present example is sized such that introducer tube (20) may be introduced to a surgical site through a trocar or other type of device. By way of example only, the outer diameter of introducer tube (20) may be between approximately 5 mm (inclusive) and approximately 15 mm (inclusive) (e.g., approximately 10 mm, etc.). Alternatively, introducer tube (20) may have any other suitable dimension.

As shown in FIGS. 3-4, a distal plug (70) is secured to the distal end of actuating rod (40). Distal plug (70) is thus translatable from a proximal position as shown in FIG. 3 to a distal position as shown in FIG. 4 by translating actuating rod (40) distally as described above. Distal plug (70) includes a resilient tab (72) that extends upwardly from distal plug (70). Resilient tab (72) is resiliently biased to extend upwardly from distal plug (70), but is movable downwardly toward distal plug (70) in order to allow distal plug (70) to fit within and translate within introducer tube (20). However, once distal plug (70) reaches the distal position shown in FIGS. 2 and 4, resilient tab (72) is configured to "snap into" side aperture (28) of introducer tube (20), such that at least a portion of resilient tab (72) protrudes into side aperture (28). With resilient tab (72) so engaged with side aperture (28), the longitudinal position of distal plug (70) may be substantially secured. In other words, engagement between resilient tab (72) and side aperture (28) may substantially prevent proximal movement of distal plug (70) once distal plug (70) has reached a distal position. Distal plug (70) may also include a recess below resilient tab (72), which may provide clearance for resilient tab (72) to deflect downwardly when distal plug (70) is proximal to the distal position shown in FIGS. 2 and 4. Such downward deflection on resilient tab (72) may be provided by the inner diameter of introducer tube (20) when distal plug (70) is proximal to the distal position shown in FIGS. 2 and 4.

One or more indentations (29) formed at distal end (26) of introducer tube (20) may also restrict distal positioning of distal plug (70). One or more indentations (29) formed at distal end (26) of introducer tube (20) may also restrict distal positioning of distal plug (70). Such restriction of distal positioning of distal plug (70) may also restrict distal positioning of actuating rod (40). In addition or in the alternative, a feature on a proximal portion of actuating rod (40) may engage handle (22) when actuating rod (40) reaches a certain distal position, to arrest further distal translation of actuating rod (40) at a selected longitudinal position. In some such versions, distal plug (70) may even be omitted. For instance, resilient hoop member (80) may be integrally secured to actuating rod (40), such that a feature located near the proximal end of tissue retrieval device (10) that arrests distal translation of actuating rod (40) may effectively also arrest distal positioning of resilient hoop member (80).

As shown in FIGS. 2-4, a resilient hoop member (80) extends distally from distal plug (70). Resilient hoop member (80) is resiliently biased to assume an outwardly expanded circular or elliptical configuration as shown in FIGS. 2 and 4. However, resilient hoop member (80) has flexibility permitting resilient hoop member (80) to compress and deformably fit within introducer tube (20) as shown in FIGS. 1 and 3. A secure attachment between resilient hoop member (80) and distal plug (70) provides unitary translation of resilient hoop member (80) and distal plug (70) relative to introducer tube (20). In addition, a secure attachment between actuating rod (40) and distal plug (70) provides unitary translation of actuating rod (40) and distal plug (70). Thus, resilient hoop member (80) may be advanced from a proximal position as shown in FIG. 3 to a distal position as shown in FIG. 4 by advancing thumb ring (42) distally toward handle (22) as described above. Such distal advancement of resilient hoop member (80) moves resilient hoop member (80) from a proximal position where it is located within introducer tube (20) to a distal position where it protrudes from open distal end (26) of introducer tube (20).

Resilient hoop member (80) may be formed of any suitable material or combination of materials, including but not limited to metal (e.g., stainless steel, nitinol, steel spring alloys, copper spring alloys, etc.), plastic, and/or metal reinforced plastic. In addition, while resilient hoop member (80) is formed as a single unitary piece, resilient hoop member (80) may alternatively be formed of any other suitable number of pieces. By way of example only, resilient hoop member (80) may be formed of two separate arms that together provide a configuration that is substantially similar to the configuration shown for resilient hoop member (80), except that the two separate arms are separated at a region corresponding to the distal-most part of resilient hoop member (80). Other suitable variations of resilient hoop member (80) will be apparent to those of ordinary skill in the art in view of the teachings herein. By way of example only, resilient hoop member (80) may be readily substituted with any bag frame component or support structure disclosed in any of the patents or patent applications cited herein. Similarly, tissue retrieval device (10) may readily incorporate any of the various bag deployment mechanisms disclosed in any of the patents or patent applications cited herein. Various suitable ways in which such alternative bag frames, support structures, deployment mechanisms, and/or other teachings in any of the patents or patent applications cited herein may be incorporated into tissue retrieval device (10) will be apparent to those of ordinary skill in the art.

Retrieval bag (60) is secured to resilient hoop member (80) in the present example. For instance, resilient hoop member (80) may be fed through slits, one or more pockets, or one or more other features near the top opening of retrieval bag (60). The engagement between retrieval bag (60) and resilient hoop member (80) is such that retrieval bag (60) translates substantially unitarily with resilient hoop member (80) relative to introducer tube (20). Thus, retrieval bag (60) may be advanced from a proximal position as shown in FIGS. 1 and 3 to a distal position as shown in FIGS. 2 and 4 by advancing thumb ring (42) distally toward handle (22) as described above. In addition, the engagement between retrieval bag (60) and resilient hoop member (80) is such that resilient hoop member (80) substantially opens the top of retrieval bag (60) when resilient hoop member (80) reaches the expanded configuration shown in FIGS. 2 and 4. While resilient hoop member (80) is flexible enough to compressingly fit within introducer tube (20), resilient hoop member (80) has sufficient rigidity to substantially support retrieval bag (60) when resilient hoop member (80) and retrieval bag (60) protrude from open distal end (26) of introducer tube (20).

Retrieval bag (60) may have any suitable configuration when retrieval bag (60) is positioned within introducer tube (20). For instance, retrieval bag (60) may be rolled up, folded up, wadded up, or have any other suitable configuration within introducer tube (20). When retrieval bag (60) has been advanced from a proximal position as shown in FIGS. 1 and 3 to a distal position as shown in FIGS. 2 and 4, a separate instrument (e.g., conventional tissue graspers, etc.) may be used to assist in unfurling retrieval bag (60). In addition or in the alternative, the material properties of retrieval bag (60) and/or gravity may cause retrieval bag (60) to at least substantially unfurl on its own once it has been deployed from introducer tube (20). With retrieval bag (60) deployed and opened as shown in FIGS. 2 and 4, a surgeon may place tissue samples or specimens, etc. (e.g., patient's gall bladder, etc.) within retrieval bag (60) for subsequent removal of such tissue samples or specimens, etc. from the patient.

In some versions, tissue retrieval device (10) may be configured such that retrieval bag (60) is removable from resilient hoop member (80) (e.g., while these components are still within the patient, etc.). Some such versions facilitate removal of retrieval bag (60) separate from removal of the other components of the tissue retrieval device (10) from the patient. For instance, in some versions tissue retrieval device (10) may include a closure string (not shown) connected to retrieval bag (60) and having a slipknot attachment to actuating rod (40). Pulling the slipknot loose from actuating rod (40) and then retracting actuating rod (40) proximally may permit detachment of retrieval bag (60) and the closure string from the other components of specimen retrieval device (10). For instance, actuating rod (40) may be fully withdrawn from introducer tube (20) and a free end of the closure string may protrude from the proximal end of introducer tube (20). In some such versions, a user may pull the closure string to close retrieval bag (60). For instance, the closure string may be engaged with retrieval bag (60) similar to a purse string. By way of example only, such a closure mechanism may be configured in accordance with the teachings of U.S. Pat. No. 6,409,733, entitled "Specimen Retrieval Bag," issued Jun. 25, 2002, the disclosure of which is incorporated by reference herein. In some such versions, retrieval bag (60) is perforated in a region between a closure string and the region where retrieval bag (60) is coupled with resilient hoop member (80). Such perforation may permit retrieval bag (60) to be separated from hoop member (80) without compromising engagement between the closure string and retrieval bag (60).

A closed retrieval bag (60) containing tissue may be removed through the same trocar through which introducer tube (20) was inserted. In particular, a closed retrieval bag (60) containing tissue may be removed through the trocar at the same time introducer tube (20) is removed from the trocar. Alternatively, introducer tube (20) may be removed from the trocar first, then the closed retrieval bag (60) containing tissue may be removed through the trocar. As yet another merely illustrative alternative, the closed retrieval bag (60) containing tissue may be removed from the patient after introducer tube (20) and the trocar have been removed from the patient. In other words, the closed retrieval bag (60) containing tissue may be removed directly through the incision through which the trocar had been previously inserted. In any of these scenarios, a protruding closure string may be used to remove retrieval bag (60) from the patient. Alternatively, retrieval bag (60) may be removed from the patient in any other suitable fashion.

In some versions, actuating rod (40) may comprise features operable with other features of introducer tube (20) or other components to prevent inadvertent retraction of actuating rod (40) during deployment of retrieval bag (60). For example, actuating rod (40) may include a one way ratcheting mechanism as described in U.S. Pat. No. 6,409,733, entitled "Specimen Retrieval Bag," issued Jun. 25, 2002, the disclosure of which is incorporated by reference herein. Other ways in which inadvertent retraction of actuating rod (40) may be avoided through various features of tissue retrieval device (10) will be apparent to those of ordinary skill in the art in view of the teachings herein. Similarly, other various suitable components, features, configurations, and functionalities of tissue retrieval device (10) will be apparent to those of ordinary skill in the art in view of the teachings herein.

Figure 5:
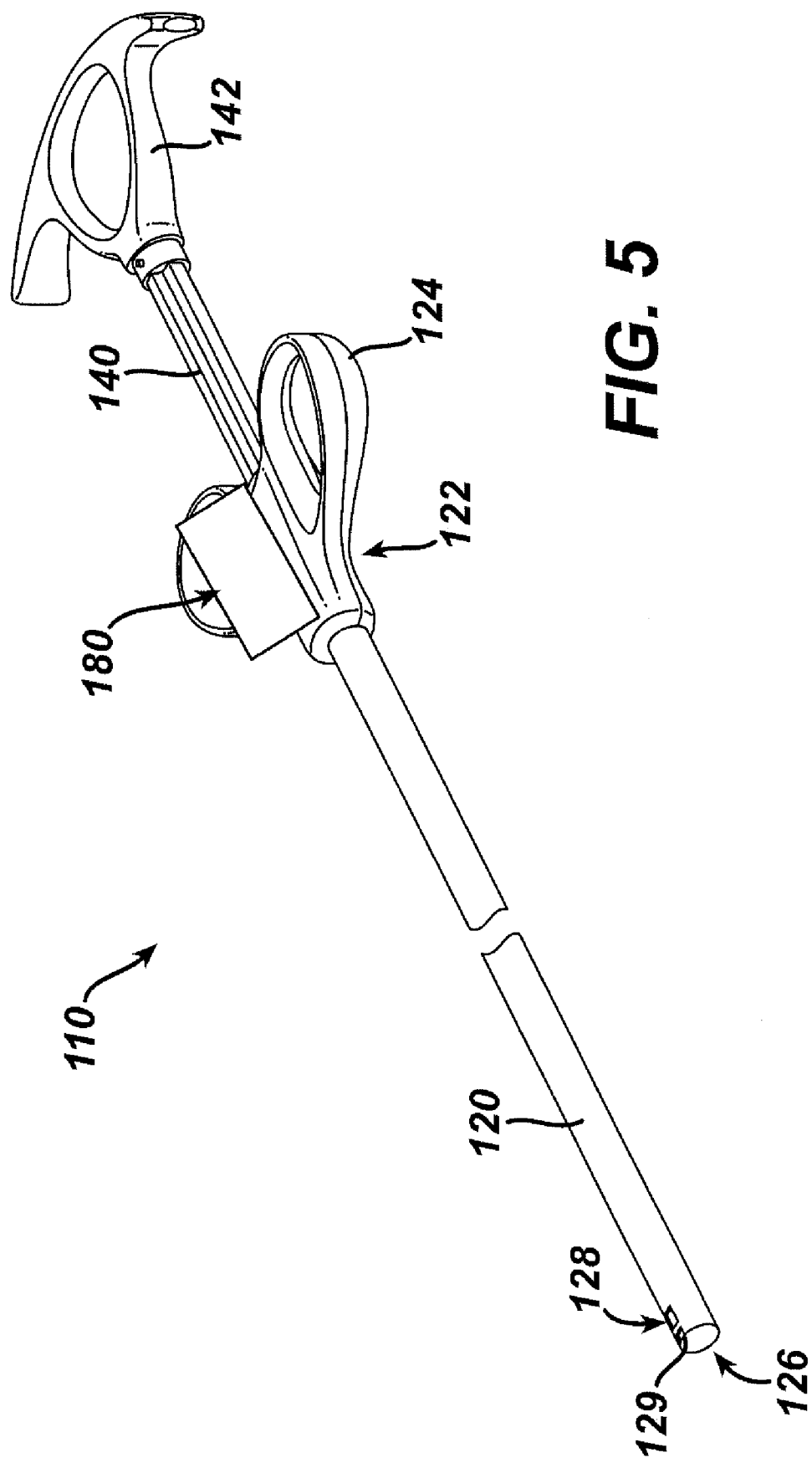
FIG. 5 is a perspective view of another exemplary tissue retrieval device, with a retrieval bag in a retracted position.
Figure 6:
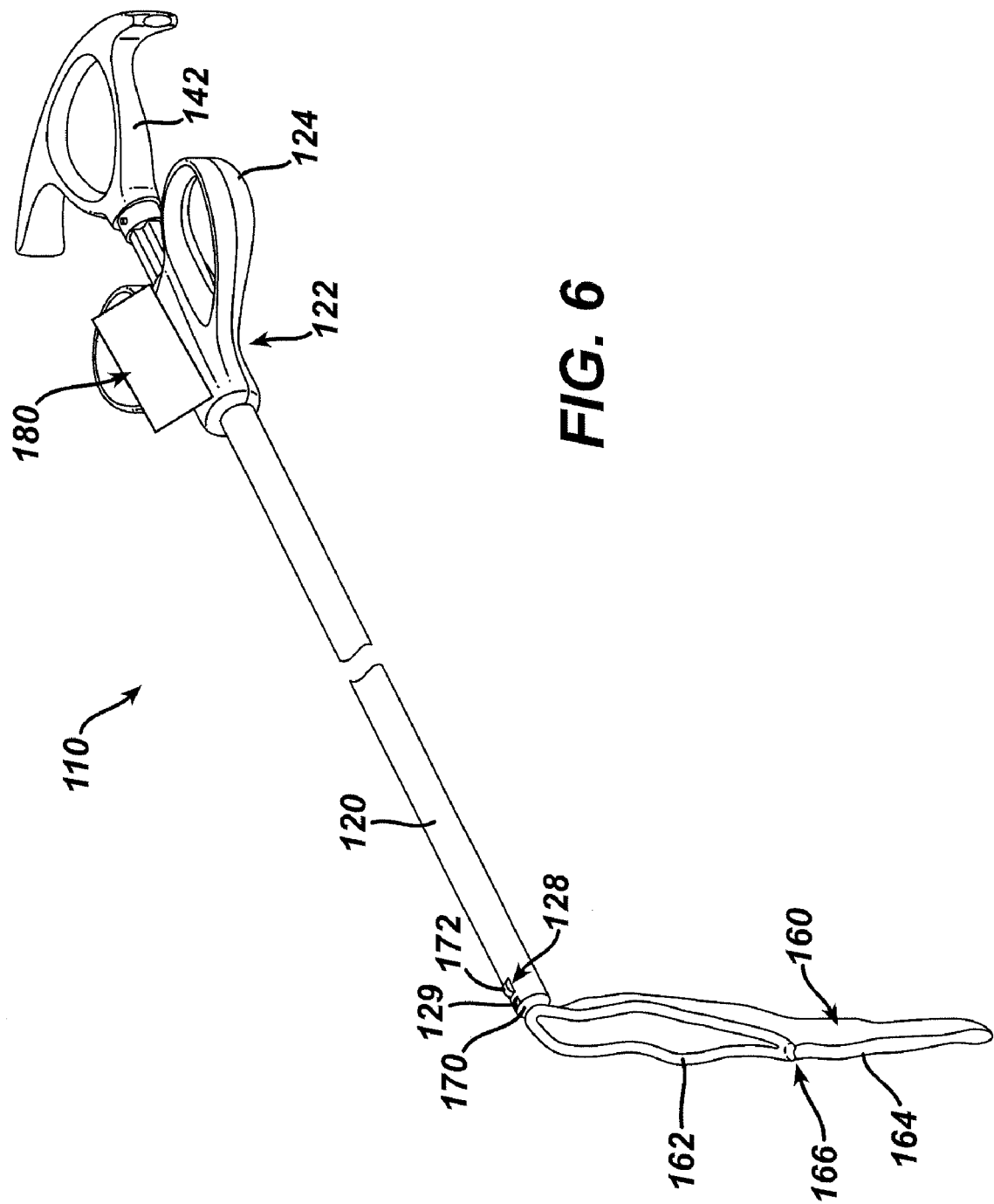
FIG. 6 is a perspective view of the tissue retrieval device of FIG. 5, with the retrieval bag in a deployed position and in an un-inflated configuration.
Figure 7:
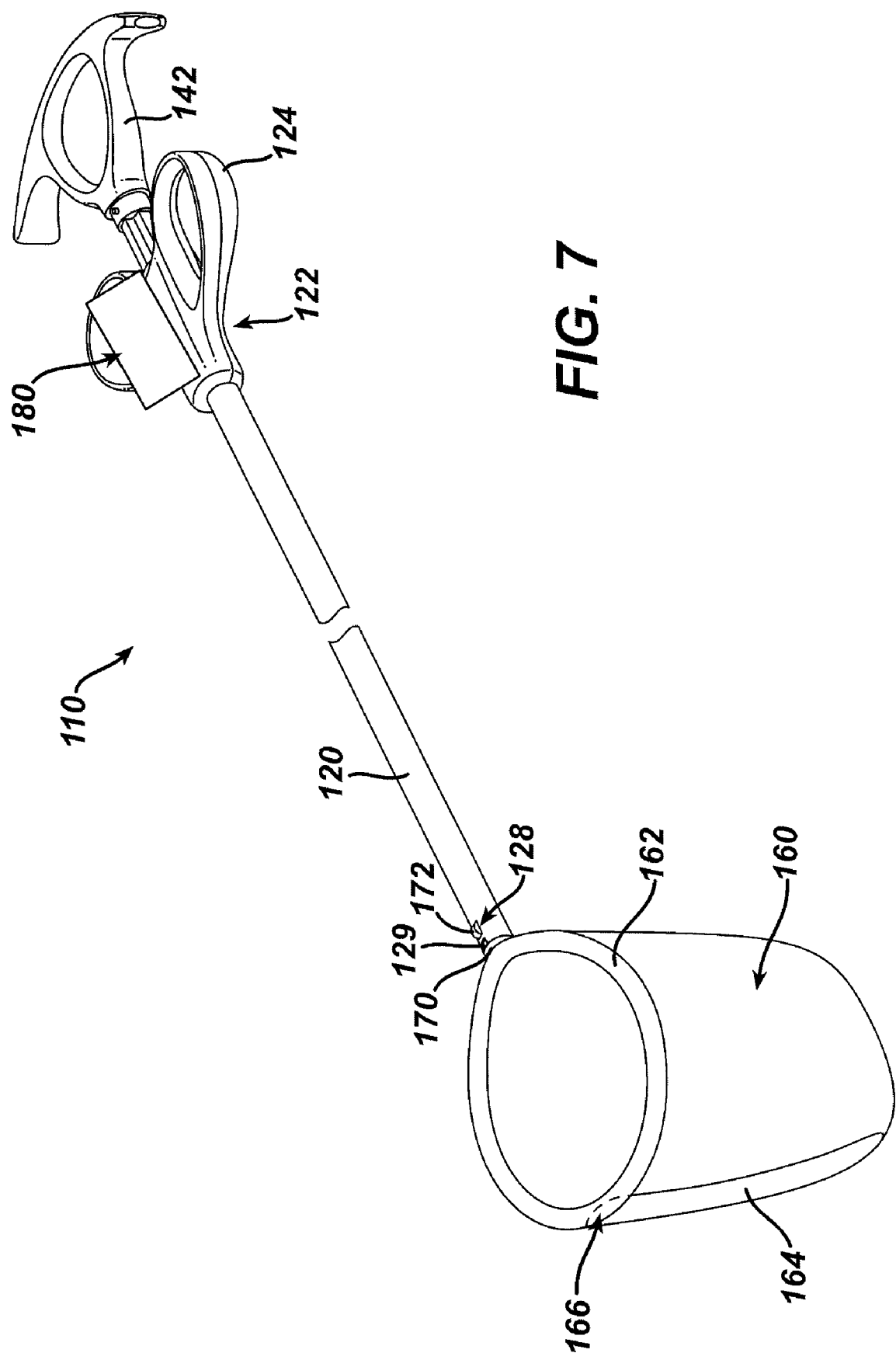
FIG. 7 is a perspective view of the tissue retrieval device of FIG. 5, with the retrieval bag in the deployed position and in an inflated configuration.

FIGS. 5-7 depict an exemplary alternative tissue retrieval device (110). Like tissue retrieval device (10) described above, tissue retrieval device (110) of this example comprises an elongate introducer tube (120), a handle (122) secured to the proximal end of introducer tube (120), an actuating rod (140), and a thumb ring (142) secured to the proximal end of actuating rod (140). Handle (122) comprises a pair of finger grips (124). Also like tissue retrieval device (10) described above, actuating rod (140) is slidable within the hollow interior of introducer tube (120) to selectively deploy a tissue retrieval bag (160) from introducer tube (120). In particular, with actuating rod (140) in a proximal position as shown in FIG. 5, a user may insert their thumb in thumb ring (142), and insert their index and middle fingers in finger grips (124), then advance thumb ring (142) distally toward finger grips (124) to translate actuating rod (140) distally to a distal position as shown in FIGS. 6-7.

In the present example introducer tube (120) is formed of metal; while handle (122), actuating rod (140), and thumb ring (142) are formed of plastic. However, it should be understood that any suitable material or combination of materials may be used to form these components and other components described herein. Introducer tube (120) has an open distal end (126) and a side aperture (128) just proximal to open distal end (126). Introducer tube (120) of the present example is sized such that introducer tube (120) may be introduced to a surgical site through a trocar or other type of device. By way of example only, the outer diameter of introducer tube (120) may be approximately between approximately 5 mm (inclusive) and approximately 15 mm (inclusive) (e.g., approximately 10 mm, etc.). Alternatively, introducer tube (120) may have any other suitable dimension.

As shown in FIGS. 6-7, a distal plug (170) is secured to the distal end of actuating rod (140). Distal plug (170) is thus translatable from a proximal position as shown in FIG. 5 to a distal position as shown in FIGS. 6-7 by translating actuating rod (140) distally as described above. Distal plug (170) includes a resilient tab (172) that extends upwardly from distal plug (170). Resilient tab (172) is resiliently biased to extend upwardly from distal plug (170), but is movable back toward distal plug (170) in order to allow distal plug (170) to fit within and translate within introducer tube (120). However, once distal plug (170) reaches the distal position shown in FIGS. 6-7, resilient tab (172) is configured to "snap into" side aperture (128) of introducer tube (120), such that at least a portion of resilient tab (172) protrudes into side aperture (128). With resilient tab (172) so engaged with side aperture (128), the longitudinal position of distal plug (170) may be substantially secured. In other words, engagement between resilient tab (172) and side aperture (128) may substantially prevent proximal movement of distal plug (170) once distal plug (170) has reached a distal position. Distal plug (170) may also include a recess below resilient tab (172), which may provide clearance for resilient tab (172) to deflect downwardly when distal plug (170) is proximal to the distal position shown in FIGS. 6-7. Such downward deflection on resilient tab (172) may be provided by the inner diameter of introducer tube (120) when distal plug (170) is proximal to the distal position shown in FIGS. 6-7.

One or more indentations (129) formed at distal end (126) of introducer tube (120) may also restrict distal positioning of distal plug (170). Such restriction of distal positioning of distal plug (170) may also restrict distal positioning of actuating rod (140). In addition or in the alternative, a feature on a proximal portion of actuating rod (140) may engage handle (122) when actuating rod (140) reaches a certain distal position, to arrest further distal translation of actuating rod (140) at a selected longitudinal position.

As shown in FIGS. 6-7, retrieval bag (160) extends distally from distal plug (170). Retrieval bag (160) includes a circumferential bladder (162) around the upper opening defined by retrieval bag (160) and a vertical bladder (164) extending along the height of retrieval bag (160). Circumferential bladder (162) is in fluid communication with vertical bladder (164) at a junction (166) that couples bladders (162, 164). Bladders (162, 164) are configured to inflate with fluid communicated from inflator (180), which will be described in greater detail below. Such inflation of bladders (162, 164) will complete the deployment and opening of retrieval bag (160) in the present example. In particular, when retrieval bag (160) is first moved to a distal position as shown in FIG. 6, retrieval bag (160) is substantially limp and may be difficult to use for containing tissue samples or specimens, etc. However, when bladders (162, 164) are inflated by inflator (180) as shown in FIG. 7, such inflated bladders (162, 164) may provide sufficient structural support to retrieval bag (160) to hold retrieval bag (160) substantially upright and open, which may in turn facilitate placement of tissue samples or specimens, etc. in retrieval bag (160).

As noted above, tissue retrieval device (110) of the present example further comprises an inflator (180). While FIGS. 5-7 show inflator (180) in block form, various suitable forms that inflator (180) may take will be apparent to those of ordinary skill in the art in view of the teachings herein. Similarly, while FIGS. 5-7 show inflator (180) as being positioned on handle (122), various other suitable locations in which inflator (180) may be positioned will be apparent to those of ordinary skill in the art in view of the teachings herein. Inflator (180) is operable to communicate a pressurized fluid or other medium to bladders (162, 164). Accordingly, tissue retrieval device (110) may include a fluid conduit (not shown) that fluidly couples bladders (162, 164) with inflator (180). Such a fluid conduit may extend along the length of introducer tube (120). Such a fluid conduit may also pass through distal plug (170). Alternatively, such a fluid conduit may couple with a separate conduit that is formed through distal plug (170), with such a separate conduit being coupled with bladders (162, 164). Such one or more conduits may provide and maintain fluid coupling between inflator (180) and bladders (162, 164) even when distal plug (170) and retrieval bag (160) are in a proximal position as shown in FIG. 5; in addition to providing fluid coupling between inflator (180) and bladders (162, 164) when distal plug (170) and retrieval bag (160) are in the distal position shown in FIG. 6. Alternatively, such one or more fluid conduits may achieve fluid coupling between inflator (180) and bladders (162, 164) only after distal plug (170) and retrieval bag (160) have reached the distal position shown in FIG. 6.

In some versions, the hollow interior of introducer tube (120) itself provides a fluid conduit between inflator (180) and bladders (162, 164). In some such versions, distal plug (170) and actuator rod (140) are both dynamically sealed within introducer tube (120), such that pressurized fluid does not escape between the interface of distal plug (170) with introducer tube (120) or the interface of actuator rod (140) and introducer tube (120). Various suitable ways in which inflator (180) and bladders (162, 164) may be fluidly coupled will be apparent to those of ordinary skill in the art in view of the teachings herein.

As noted above, inflator (180) may take a variety of forms. By way of example only, inflator (180) may comprise a manually operable air pump. For instance, such an air pump may include a reciprocatable plunger that is operable to pump air into bladders (162, 164). Such a pump may be configured to substantially fill bladders (162, 164) with a single stroke of the plunger or after multiple strokes of the plunger. Alternatively, inflator (180) may be operable to pump some other kind of gas or some kind of liquid (e.g., saline, etc.) into bladders (162, 164). As another merely illustrative example, inflator (180) may comprise a cartridge of a pressurized medium (e.g., air, liquid, some other type of fluid, etc.). In some such versions, inflator (180) includes a feature that is operable to pierce the cartridge or otherwise release at least a portion of the pressurized medium within the cartridge to reach bladders (162, 164). As yet another merely illustrative example, inflator (180) may simply comprise a port that allows an external source of a pressurized medium to be coupled with tissue retrieval device (110) to inflate bladders (162, 164). Still other suitable forms that inflator (180) may take will be apparent to those of ordinary skill in the art in view of the teachings herein.

It should also be understood that inflator (180) may also be used to advance distal plug (170) from the proximal position to the distal position. Thus, actuating rod (140) may be omitted. As another variation, actuating rod (140) may form part of inflator (180). For instance, the distal end of actuating rod (140) may include a piston head that is dynamically sealed to the inner diameter of introducer tube (120) and that is spaced apart from distal plug (170). Distal plug (170) may be separately slidable within introducer tube (120) and may also be dynamically sealed to the inner diameter of introducer tube (120). Thus, distal plug (170) may be advanced distally by pressurization of the air between the piston at the end of actuating rod (140) and distal plug (170) upon distal advancement of actuating rod (140). Further distal advancement of actuating rod (140) may inflate bladders (162, 164) by distal positioning of the piston at the distal end of actuating rod (140), particularly when distal plug (170) is locked at a distal position by engagement between resilient tab (172) and side aperture (128). In some such versions, a ratcheting mechanism or some other feature may allow actuating rod (140) to be locked in a distal position to substantially maintain the fluid pressure within inflated bladders (162, 164). Such a locking mechanism or feature may be unlocked when tissue has been placed in retrieval bag (160), allowing actuating rod (140) to be withdrawn, which may in turn evacuate fluid from bladders (162, 164).

In some variations of tissue retrieval device (110), resilient hoop member (80) of tissue retrieval device (10) is coupled with distal plug (170) of tissue retrieval device (110). For instance, resilient hoop member (80) may be fed through circumferential bladder (162) of tissue retrieval bag (160). Alternatively, circumferential bladder (162) may be omitted from tissue retrieval bag (160). To the extend that circumferential bladder (162) is omitted, some other conduit may be provided in tissue retrieval bag (160) to provide fluid communication from inflator (180) to vertical bladder (164). Thus, in some such versions, resilient hoop member (80) is used to open the top portion of tissue retrieval bag (160) upon deployment of tissue retrieval bag (160) from the open distal end (126) of introducer tube (120); while vertical bladder (164) is inflated to unfurl or otherwise complete the opening of tissue retrieval bag (160). It should therefore be understood that a resilient hoop member (80) (or some similar component(s), etc.) may be used in conjunction with an inflator (180). Various examples that combine a resilient hoop member (80) with an inflator (180) will be described in greater detail below, while other examples will be apparent to those of ordinary skill in the art in view of the teachings herein.

In some versions, tissue retrieval device (110) may be configured such that retrieval bag (160) is removable from distal plug (170) (e.g., while these components are still within the patient, etc.). Some such versions facilitate removal of retrieval bag (160) separate from removal of the other components of the tissue retrieval device (110) from the patient. For instance, in some versions tissue retrieval device (110) may include a closure string (not shown) connected to retrieval bag (160) and having a slipknot attachment to actuating rod (140). Pulling the slipknot loose from actuating rod (140) and then retracting actuating rod (140) proximally may permit detachment of retrieval bag (160) and the closure string from the other components of specimen retrieval device (110). For instance, actuating rod (140) may be fully withdrawn from introducer tube (120) and a free end of the closure string may protrude from the proximal end of introducer tube (120). In some such versions, a user may pull the closure string to close retrieval bag (160). For instance, the closure string may be engaged with retrieval bag (160) similar to a purse string. By way of example only, such a closure mechanism may be configured in accordance with the teachings of U.S. Pat. No. 6,409,733, entitled "Specimen Retrieval Bag," issued Jun. 25, 2002, the disclosure of which is incorporated by reference herein.

As another merely illustrative variation, retrieval bag (160) may be configured such that retrieval bag (160) substantially closes upon evacuation of fluid from bladders (162, 164). For instance, such fluid evacuation may suffice to sufficiently close retrieval bag (160) without an additional closure string or other feature being used to close retrieval bag (160). By way of example only, the material forming retrieval bag (160) may be resiliently biased to close retrieval bag (160), such that retrieval bag (160) opens against this resilient bias when bladders (162, 164) are inflated. Of course, even in versions where a closure string or other feature is used to close retrieval bag (160), fluid may still be evacuated from bladders (162, 164) as part of the process of closing retrieval bag. A closed retrieval bag (160) containing tissue may be removed from the patient in accordance with any of the above teachings relating to the removal of a closed retrieval bag (60) containing tissue. Alternatively, retrieval bag (160) may be removed from the patient in any other suitable fashion.

In some versions, actuating rod (140) may comprise features operable with other features of introducer tube (120) or other components to prevent inadvertent retraction of actuating rod (140) during deployment of retrieval bag (160). For example, actuating rod (140) may include a one way ratcheting mechanism as described in U.S. Pat. No. 6,409,733, entitled "Specimen Retrieval Bag," issued Jun. 25, 2002, the disclosure of which is incorporated by reference herein. Other ways in which inadvertent retraction of actuating rod (140) may be avoided through various features of tissue retrieval device (110) will be apparent to those of ordinary skill in the art in view of the teachings herein. Similarly, other various suitable components, features, configurations, and functionalities of tissue retrieval device (110) will be apparent to those of ordinary skill in the art in view of the teachings herein.

In some alternative versions, tissue retrieval device (10, 110) lacks actuating rod (40, 140) altogether. In some such versions, the position of distal plug (70, 170) in introducer tube (20, 120) is substantially fixed. In addition, an external sheath or tube (not shown) is slidably positioned about introducer tube (20, 120). For instance, in the case of tissue retrieval device (10), such an external sheath may be distally positioned to encompass resilient hoop member (80) and retrieval bag (60) as tissue retrieval device (10) is being inserted in a patient; then the external sheath may be proximally retracted relative to introducer tube (20) to expose resilient hoop member (80) and retrieval bag (60) within the patient. Similarly, in the case of tissue retrieval device (110), such an external sheath may be distally positioned to encompass retrieval bag (160) as tissue retrieval device (110) is being inserted in a patient; then the external sheath may be proximally retracted relative to introducer tube (120) to expose retrieval bag (160) within the patient. In either case, such an external sheath may extend proximally enough to allow the external sheath to be externally manipulated by a surgeon. For instance, a proximal end of the external sheath may include a handle portion near handle (22, 122) of introducer tube (20, 120).

Figure 8:
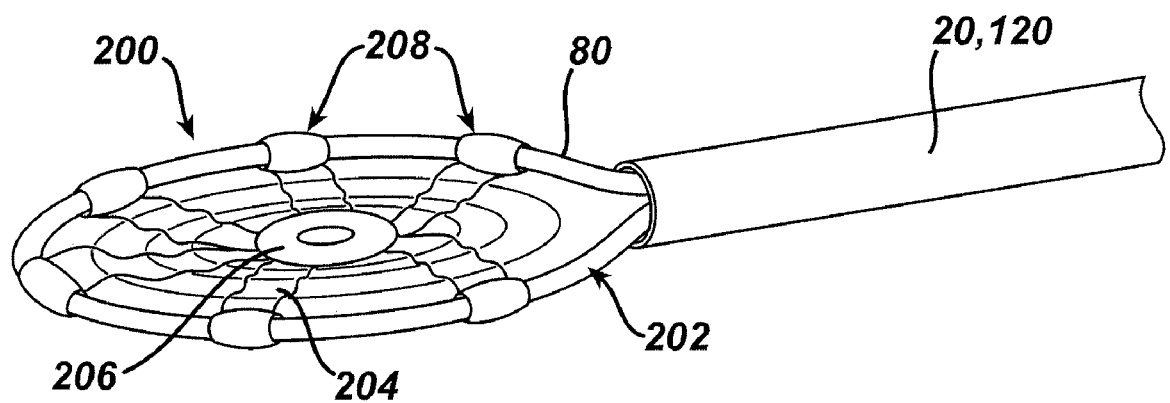
FIG. 8 is a perspective view of an exemplary alternative retrieval bag, in a deployed position and in an un-inflated configuration.
Figure 9:
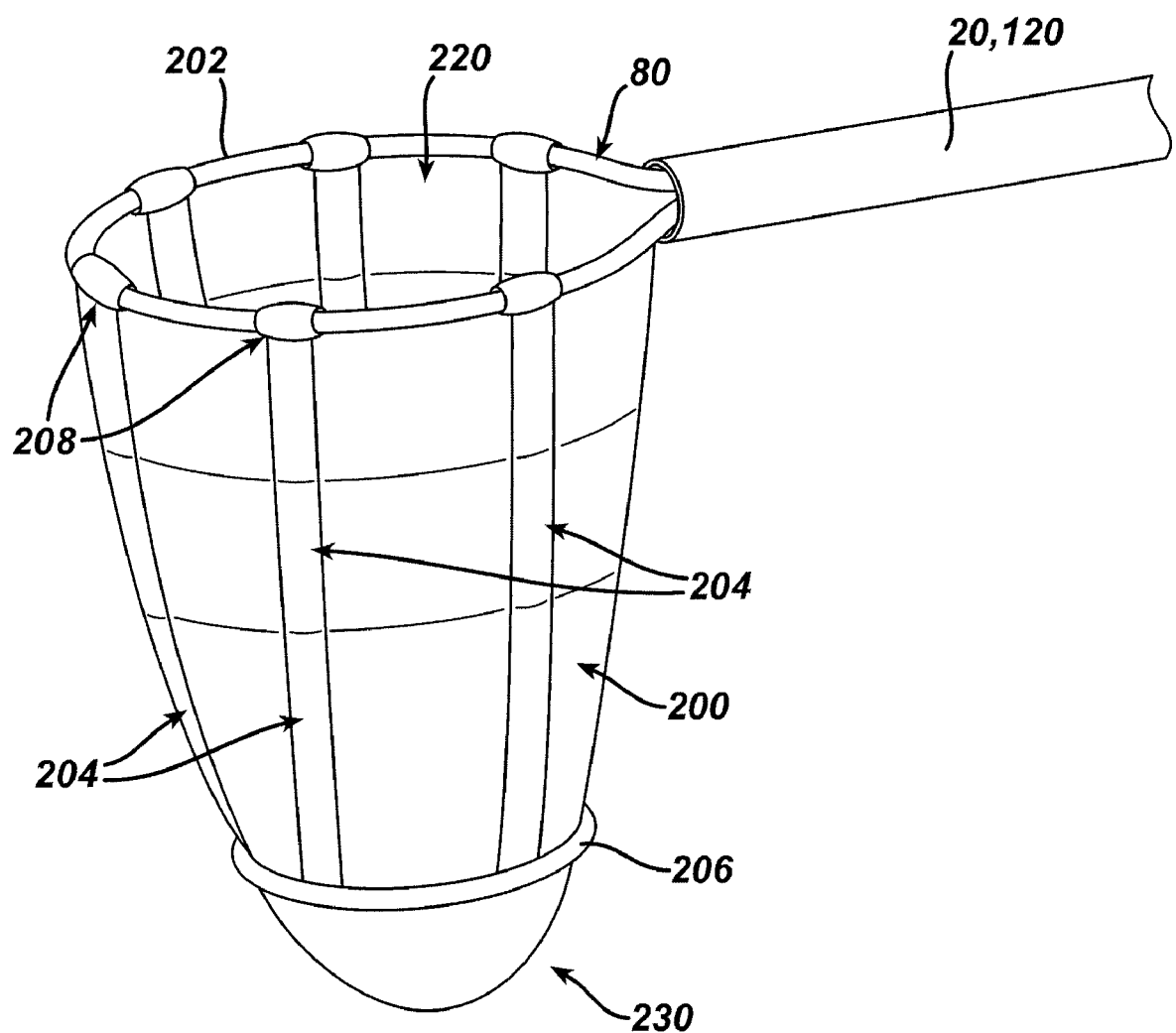
FIG. 9 is a perspective view of the retrieval bag of FIG. 8, in an inflated configuration.

FIGS. 8-15 show various alternative tissue retrieval bags (200, 300, 400, 500) that may be coupled with tissue retrieval device (10), tissue retrieval device (110), a hybrid of tissue retrieval devices (10, 110), or some other type of tissue retrieval device. For instance, FIGS. 8-9 show a tissue retrieval bag (200) that is secured to a resilient hoop member (80) and that has integral bladders (202, 204, 206). In particular, retrieval bag (200) includes an upper circumferential bladder (202) extending about the perimeter of the top opening (220) defined by retrieval bag (200); a plurality of vertical rib bladders (204) extending along a substantial portion of the length of retrieval bag (200); and a lower circumferential bladder (206) extending about the perimeter of a bottom portion (230) of retrieval bag (200). Bladders (202, 204, 206) are all in fluid communication with each other. In particular, upper circumferential bladder (202) is coupled with the top ends of rib bladders (204) at nodes (208); while the lower ends of rib bladders (204) terminate at lower circumferential bladder (206).

Retrieval bag (200) may be initially retracted within introducer tube (20, 120), much like the configurations shown in FIGS. 1 and 5. Introducer tube (20, 120) may then be inserted into a patient (e.g., via a trocar, natural orifice, incision, etc.). Retrieval bag (200) may then be advanced to a distal position as shown in FIG. 8. Such distal advancement of retrieval bag (200) may be accomplished in accordance with any of the explicit teachings herein or using any suitable components, structures, features, or techniques that may be apparent to one of ordinary skill in the art in view of the teachings herein. By way of example only, an actuation rod (40, 140) may be advanced distally relative to introducer tube (20, 120) to distally expose retrieval bag (200) relative to introducer tube (20, 120). As another merely illustrative example, a sheath about introducer tube (20, 120) may be retracted proximally relative to introducer tube (20, 120) to reveal retrieval bag (200). The resilience of resilient hoop member (80) may place retrieval bag (200) in the position shown in FIG. 8. Alternatively, retrieval bag (200) may be substantially limp at this stage, similar to retrieval bag (160) shown in FIG. 6 (e.g., where resilient hoop member (80) is omitted, etc.). In some versions, with retrieval bag (200) exposed as shown in FIG. 8, the material forming retrieval bag (200) is resiliently biased to provide the substantially flat configuration of retrieval bag (200) as shown in FIG. 8.

With retrieval bag (200) exposed as shown in FIG. 8, bladders (202, 204, 206) are inflated by inflator (180). In particular, inflator (180) forces a fluid medium (e.g., air, some other gas, saline, some other liquid, etc.) into bladders (202, 204, 206) to substantially fill bladders (202, 204, 206). As described above, inflator (180) may comprise some component secured to handle (22, 122). Alternatively, inflator (180) may be formed by a piston within introducer tube (20, 120)

that may be advanced distally to inflate bladders (202, 204, 206). Other suitable ways in which bladders (202, 204, 206) may be inflated will be apparent to those of ordinary skill in the art in view of the teachings herein. As bladders (202, 204, 206) are inflated, retrieval bag (200) expands or otherwise extends downward to reach the configuration shown in FIG. 9. In the configuration shown in FIG. 9, bottom portion (230) of retrieval bag (200) is substantially separated from top opening (220) of retrieval bag (200), such that retrieval bag (200) provides an open volume for receiving a tissue sample or specimen, etc.

Once a tissue sample or specimen, etc. has been placed in retrieval bag (200), retrieval bag (200) may be closed in various ways. For instance, fluid may be evacuated from bladders (202, 204, 206). Such evacuation of fluid from bladders (202, 204, 206) may be accomplished by simply reversing whatever action was induced in inflator (180) to inflate bladders (202, 204, 206). Alternatively, bladders (202, 204, 206) may simply be vented to allow pressurized fluid to escape from bladders (202, 204, 206). Other suitable ways in which fluid may be evacuated from bladders (202, 204, 206) will be apparent to those of ordinary skill in the art in view of the teachings herein. In some versions, the evacuation of fluid from bladders (202, 204, 206) is sufficient to substantially close retrieval bag (200). For instance, the material properties (e.g., resilient bias, etc.) of retrieval bag (200) may cause retrieval bag (200) to shrink upon evacuation of fluid from bladders (202, 204, 206), which may in turn substantially close retrieval bag (200). In addition or in the alternative, retrieval bag (200) may incorporate a closure string as described above, a belt, a cable tie, or some other cinching feature. Other suitable ways in which retrieval bag (200) may be closed will be apparent to those of ordinary skill in the art in view of the teachings herein. Once retrieval bag (200) has been sufficiently closed, retrieval bag (200) may be removed from the patient in accordance with any of the above teachings relating to the removal of a closed retrieval bag (60) containing tissue. Alternatively, retrieval bag (200) may be removed from the patient in any other suitable fashion.

While rib bladders (204) are shown as being substantially vertical and running along a substantial portion of the length of retrieval bag (200), it should be understood that rib bladders (204) may alternatively have any other suitable length and shape. For instance, rib bladders (204) may instead have a helical orientation. Similarly, while retrieval bag (200) of the present example has six rib bladders (204), it should be understood that any other suitable number of rib bladders (204) may be used. For instance, retrieval bag (200) may have just one or two rib bladders (204) in some versions. Still other suitable variations of retrieval bag (200), including but not limited to alternative components, features, configurations, and functionalities, will be apparent to those of ordinary skill in the art in view of the teachings herein.

Figure 11:
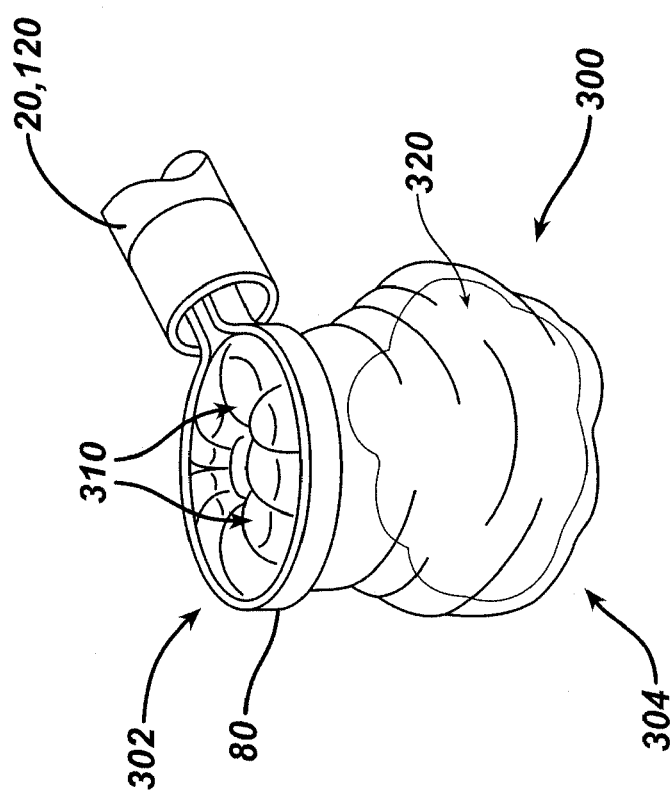
FIG. 11 is a perspective view of the retrieval bag of FIG. 10, in an inflated configuration.
Figure 10:
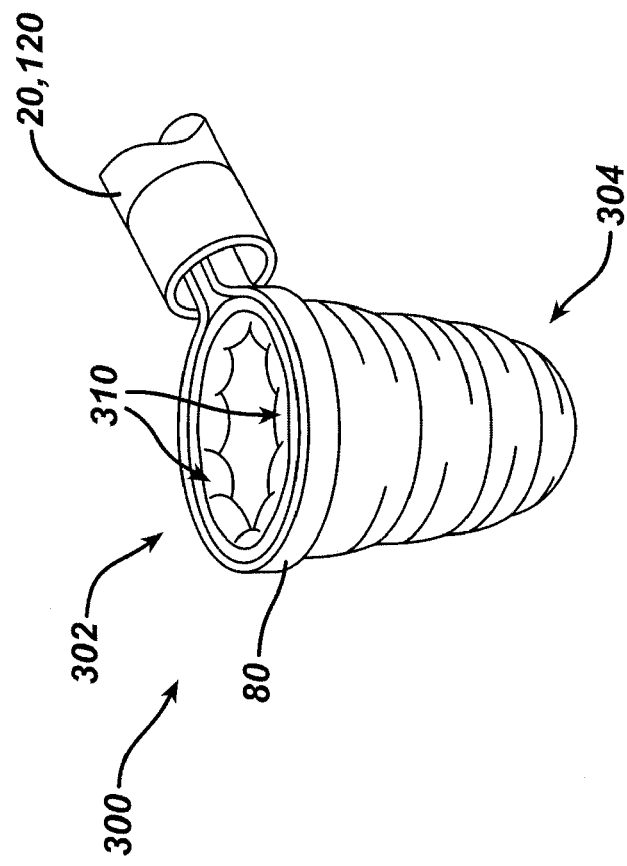
FIG. 10 is a perspective view of another exemplary alternative retrieval bag, in a deployed position and in an un-inflated configuration.

FIGS. 10-11 show another exemplary tissue retrieval bag (300). Retrieval bag (300) of this example is secured to a resilient hoop member (80) and has a bi-layer construction. Retrieval bag (300) has an open end (302) and a closed end (304). Open end (302) provides an entry permitting the placement of material (320) (e.g., a tissue specimen, etc.) into retrieval bag (300). The bi-layer construction of retrieval bag (300) permits inflation of retrieval bag (300) with a fluid (e.g., air, saline, etc.) between the two layers, to substantially seal material (320) within retrieval bag (300). In particular, FIGS. 10-11 show a bi-layer construction that forms an annular fluid pocket (310) at open end (302) of retrieval bag (300). Pocket (310) is formed between the two adjacent layers of retrieval bag (300) in the present example. For instance, the two adjacent layers of retrieval bag (300) may be substantially secured to each other in regions below fluid pocket (310); whereas fluid pocket (310) is formed by such two adjacent layers being not secured to each other in the region of fluid pocket (310). The regions of the two layers that are secured together may be secured together in any suitable fashion, including but not limited to using adhesives, welding, heat-sealing, or using any other suitable techniques. In some other versions, pocket (310) comprises an annular bladder that is secured to an inner layer of retrieval bag (300) or between layers of retrieval bag (300).

Retrieval bag (300) may be initially retracted within introducer tube (20, 120), much like the configurations shown in FIGS. 1 and 5. Introducer tube (20, 120) may then be inserted into a patient (e.g., via a trocar, natural orifice, incision, etc.). Retrieval bag (300) may then be advanced to a distal position as shown in FIG. 10. Such distal advancement of retrieval bag (300) may be accomplished in accordance with any of the explicit teachings herein or using any suitable components, structures, features, or techniques that may be apparent to one of ordinary skill in the art in view of the teachings herein. By way of example only, an actuation rod (40, 140) may be advanced distally relative to introducer tube (20, 120) to distally expose retrieval bag (300) relative to introducer tube (20, 120). As another merely illustrative example, a sheath about introducer tube (20, 120) may be retracted proximally relative to introducer tube (20, 120) to reveal retrieval bag (300). The resilience of resilient hoop member (80) may place retrieval bag (300) in the position shown in FIG. 10.

With retrieval bag (300) in the open position as shown in FIG. 10, material (320) may be placed in open end (302) of retrieval bag (300). A fluid medium (e.g., air, saline, etc.) may then be introduced into fluid pocket (310) formed between the layers of retrieval bag (300). For instance, inflator (180) may be used to force a fluid medium into fluid pocket (310) to substantially fill fluid pocket (310). As described above, inflator (180) may comprise some component secured to handle (22, 122). Alternatively, inflator (180) may be formed by a piston within introducer tube (20, 120) that may be advanced distally to inflate fluid pocket (310). Other suitable ways in which fluid pocket (310) may be inflated will be apparent to those of ordinary skill in the art in view of the teachings herein. As shown in FIG. 11, inflated fluid pocket (310) substantially encloses material (320) within retrieval bag (300). In some versions, inflated fluid pocket (310) substantially seals material (320) within retrieval bag (300). In addition or in the alternative, retrieval bag (300) may incorporate a closure string as described above, a belt, a cable tie, or some other cinching feature. Other suitable ways in which retrieval bag (300) may be closed will be apparent to those of ordinary skill in the art in view of the teachings herein. Once retrieval bag (300) has been sufficiently closed, retrieval bag (300) may be removed from the patient in accordance with any of the above teachings relating to the removal of a closed retrieval bag (60) containing tissue. Alternatively, retrieval bag (300) may be removed from the patient in any other suitable fashion.

In the present example, fluid pocket (310) is formed only near open end (302) of retrieval bag (300). For instance, fluid pocket (310) only extends slightly below resilient hoop member (80) in the present example. In the example shown in FIGS. 10-11, the size and position of fluid pocket (310) is such that inflated pocket (310) does not bear against material (320) in retrieval bag (300). However, it should be understood that fluid pocket (310) may extend any other suitable distance below resilient hoop member (80), and may bear against material (320) in bag (300) when fluid pocket (310) is inflated. For instance, as will be described in greater detail below with reference to FIGS. 12-13, a fluid pocket may alternatively extend the full length of a retrieval bag. It should also be understood that, while fluid pocket (310) of the present example has a substantially annular shape, fluid pocket (310) may have any suitable shape. Furthermore, while just one fluid pocket (310) is provided in retrieval bag (300), other versions of retrieval bag (300) may include any other suitable number of fluid pockets (310) in any suitable locations.

Figure 12:
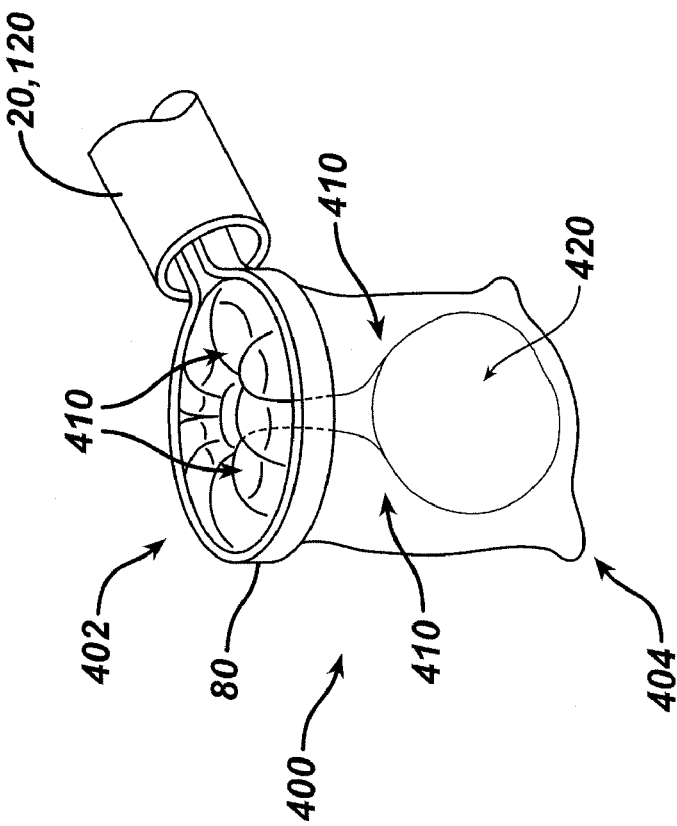
FIG. 12 is a perspective view of another exemplary alternative retrieval bag, in a deployed position and in an un-inflated configuration.
Figure 13:
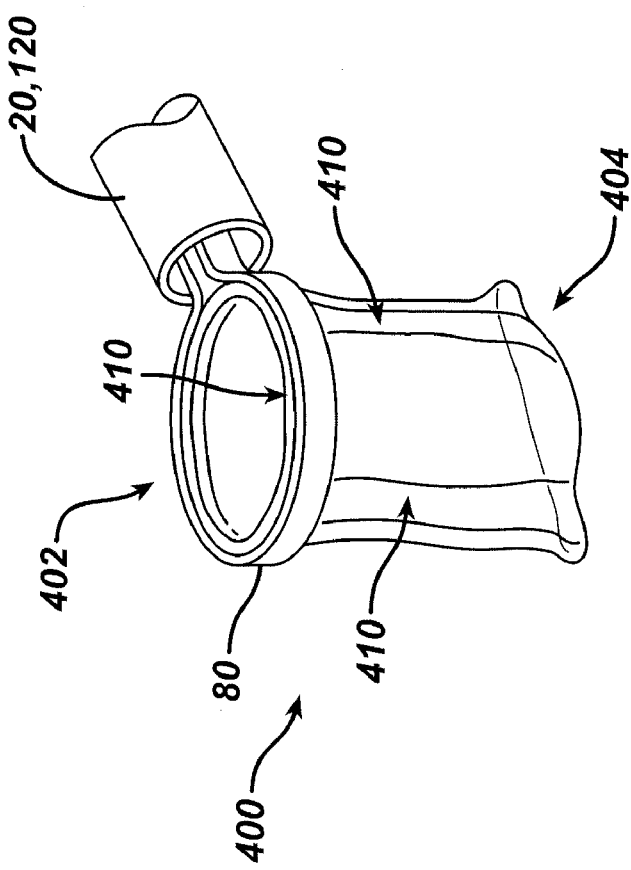
FIG. 13 is a perspective view of the retrieval bag of FIG. 12, in an inflated configuration.

FIGS. 12-13 show yet another exemplary retrieval bag (400). Retrieval bag (400) of this example is substantially identical to retrieval bag (300) above. Retrieval bag (400) of this example is also secured to a resilient hoop member (80) and has a bi-layer construction. Retrieval bag (400) has an open end (402) and a closed end (404). Open end (402) provides an entry permitting the placement of material (420) (e.g., a tissue specimen, etc.) into retrieval bag (400). The bi-layer construction of retrieval bag (400) permits inflation of retrieval bag (400) with a fluid (e.g., air, saline, etc.) between the two layers, to substantially seal material (420) within retrieval bag (400). In particular, FIGS. 12-13 show a bi-layer construction that forms a fluid pocket (410) that extends about the full perimeter and length of retrieval bag (400). This bi-layer construction is provided by an inner layer that is substantially separate from an outer layer, and which has a length approximately equal to (or greater than) the length of the outer layer.

Retrieval bag (400) may be initially retracted within introducer tube (20, 120), much like the configurations shown in FIGS. 1 and 5. Introducer tube (20, 120) may then be inserted into a patient (e.g., via a trocar, natural orifice, incision, etc.). Retrieval bag (400) may then be advanced to a distal position as shown in FIG. 12. Such distal advancement of retrieval bag (400) may be accomplished in accordance with any of the explicit teachings herein or using any suitable components, structures, features, or techniques that may be apparent to one of ordinary skill in the art in view of the teachings herein. By way of example only, an actuation rod (40, 140) may be advanced distally relative to introducer tube (20, 120) to distally expose retrieval bag (400) relative to introducer tube (20, 120). As another merely illustrative example, a sheath about introducer tube (20, 120) may be retracted proximally relative to introducer tube (20, 120) to reveal retrieval bag (400). The resilience of resilient hoop member (80) may place retrieval bag (400) in the position shown in FIG. 12.

With retrieval bag (400) in the open position as shown in FIG. 12, material (420) may be placed in open end (402) of retrieval bag (400). A fluid medium (e.g., air, saline, etc.) may then be introduced into fluid pocket (410) formed between the layers of retrieval bag (400). For instance, inflator (180) may be used to force a fluid medium into fluid pocket (410) to substantially fill fluid pocket (410). As described above, inflator (180) may comprise some component secured to handle (22, 122). Alternatively, inflator (180) may be formed by a piston within introducer tube (20, 120) that may be advanced distally to inflate fluid pocket (410). Other suitable ways in which fluid pocket (410) may be inflated will be apparent to those of ordinary skill in the art in view of the teachings herein. As shown in FIG. 13, inflated fluid pocket (410) substantially encloses material (420) within retrieval bag (400). In some versions, inflated fluid pocket (410) substantially seals material (420) within retrieval bag (400). In addition or in the alternative, retrieval bag (400) may incorporate a closure string as described above, a belt, a cable tie, or some other cinching feature. Other suitable ways in which retrieval bag (400) may be closed will be apparent to those of ordinary skill in the art in view of the teachings herein. Once retrieval bag (400) has been sufficiently closed, retrieval bag (400) may be removed from the patient in accordance with any of the above teachings relating to the removal of a closed retrieval bag (60) containing tissue. Alternatively, retrieval bag (400) may be removed from the patient in any other suitable fashion.

In some versions, at least a portion of the bottom part of the inner layer of retrieval bag (400) is secured to the bottom part of the outer layer of retrieval bag (400). For instance, such a connection may be in the form of a spot, line, or any other suitable type of connection. Furthermore, such a connection may be provided by an adhesive, welding, heat-sealing, and/or using any other suitable techniques. Such a connection may prevent the inner layer of retrieval bag (400) from turning inside-out when fluid pocket is inflated (410), which might otherwise result in inadvertent expulsion of material (420) from retrieval bag.

Figure 14:
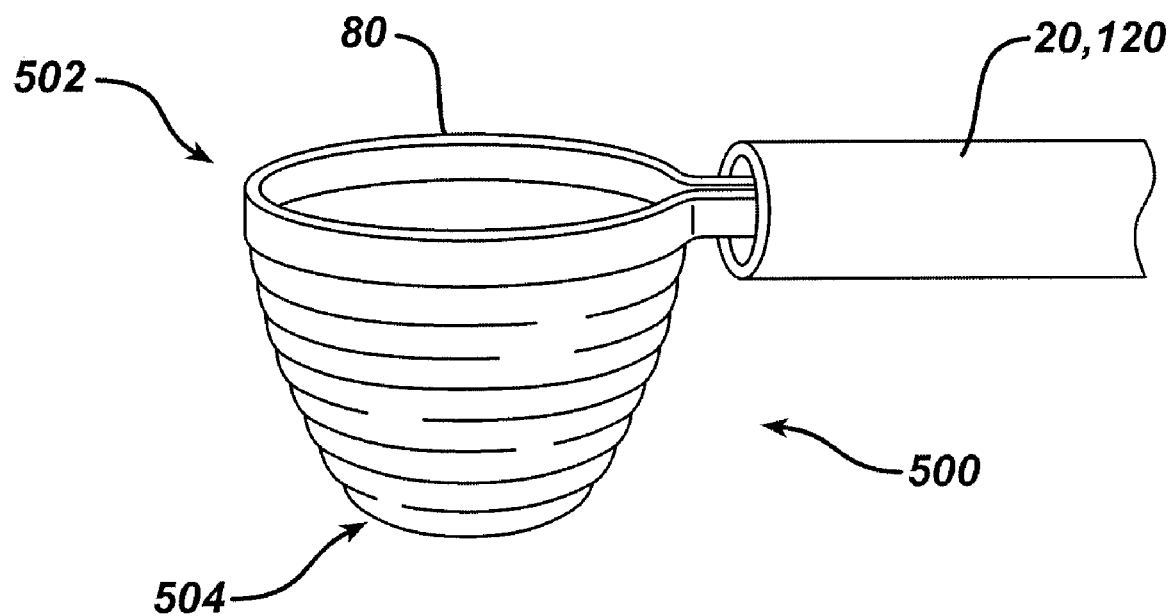
FIG. 14 is a perspective view of another exemplary tissue retrieval bag, in an unexpanded configuration.
Figure 15:
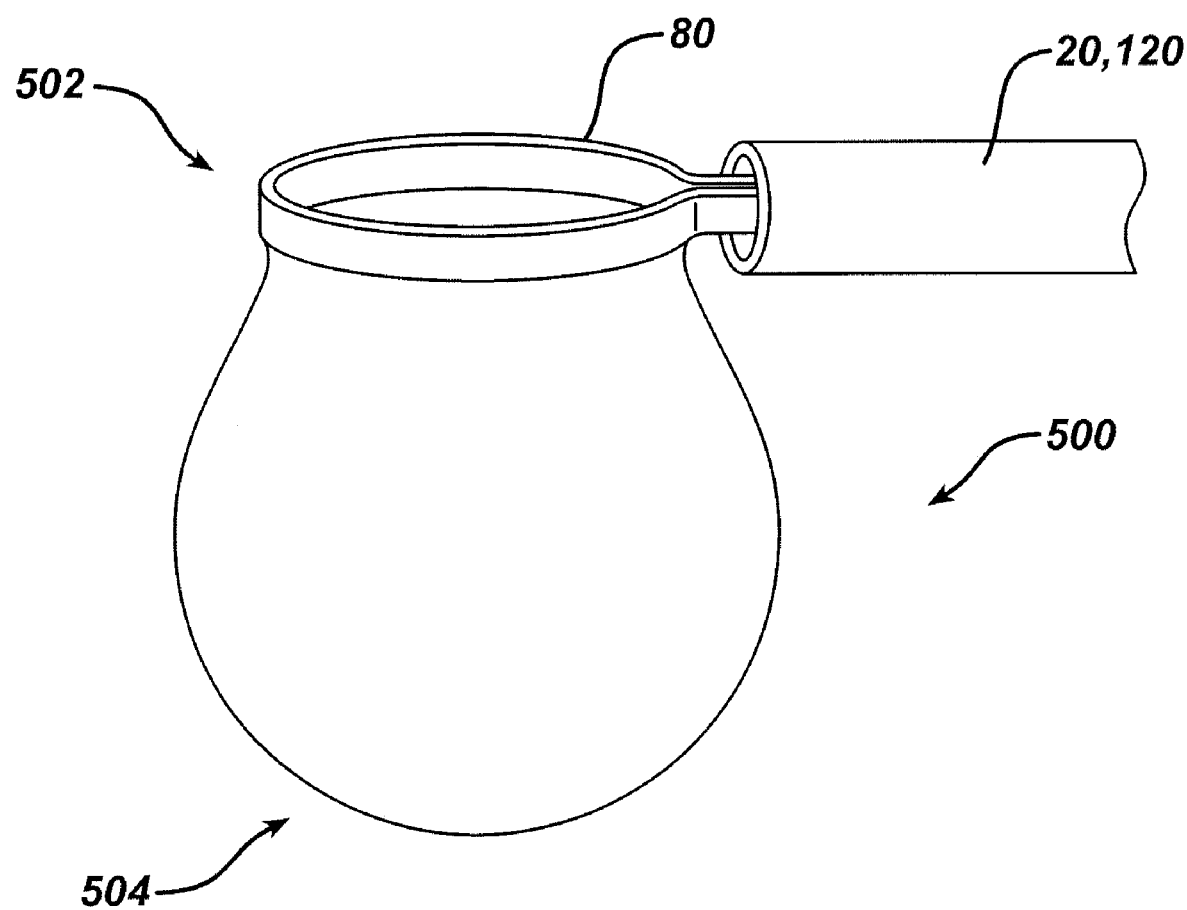
FIG. 15 is a perspective view of the tissue retrieval bag of FIG. 14, in an expanded configuration.

FIGS. 14-15 illustrate yet another exemplary retrieval bag (500). Retrieval bag (500) of this example is secured to a resilient hoop member (80). Retrieval bag (500) has an open end (502) and a closed end (504). Open end (502) provides an entry permitting the placement of material (e.g., a tissue specimen, etc.) into retrieval bag (500). In this example, retrieval bag (500) is formed of a material that is sensitive to an environmental condition that causes retrieval bag (500) to expand from a contracted position as shown in FIG. 14 to an expanded position as shown in FIG. 15. For instance, retrieval bag (500) may be responsive to carbon dioxide, water, temperature exceeding a threshold, or other environmental conditions that may be present within a patient's body. By way of example only, retrieval bag (500) may be formed in whole or in part by nitinol, gelatin, bovine, environmentally sensitive plastics, sponges, polymerized hydrogels, etc., including combinations thereof. Still other suitable materials (and combinations of materials) that may be used to form retrieval bag (500) (in whole or in part) will be apparent to those of ordinary skill in the art in view of the teachings herein.

Retrieval bag (500) may be initially retracted within introducer tube (20, 120), much like the configurations shown in FIGS. 1 and 5. Introducer tube (20, 120) may then be inserted into a patient (e.g., via a trocar, natural orifice, incision, etc.). Retrieval bag (500) may then be advanced to a distal position as shown in FIG. 14. Such distal advancement of retrieval bag (500) may be accomplished in accordance with any of the explicit teachings herein or using any suitable components, structures, features, or techniques that may be apparent to one of ordinary skill in the art in view of the teachings herein. By way of example only, an actuation rod (40, 140) may be advanced distally relative to introducer tube (20, 120) to distally expose retrieval bag (500) relative to introducer tube (20, 120). As another merely illustrative example, a sheath about introducer tube (20, 120) may be retracted proximally relative to introducer tube (20, 120) to reveal retrieval bag (500). The resilience of resilient hoop member (80) may place retrieval bag (500) in the position shown in FIG. 14.

With retrieval bag (500) in the open position as shown in FIG. 14 and being exposed within the patient's body, some environmental condition within the patient's body (e.g., heat, water, carbon dioxide from insufflation, etc.) and/or an elastic property of the material forming retrieval bag (500) causes the material forming retrieval bag (500) to expand to the size shown in FIG. 15. This expanded configuration of retrieval bag (500) may permit retrieval bag (500) to accept and accommodate a relatively greater volume of material (e.g., tissue specimen, etc.) within retrieval bag (500). After material has been placed in retrieval bag (500), retrieval bag (500)

may be closed using a closure string as described above, a belt, a cable tie, or some other cinching feature. Other suitable ways in which retrieval bag (500) may be closed will be apparent to those of ordinary skill in the art in view of the teachings herein. Once retrieval bag (500) has been sufficiently closed, retrieval bag (500) may be removed from the patient in accordance with any of the above teachings relating to the removal of a closed retrieval bag (60) containing tissue. Alternatively, retrieval bag (500) may be removed from the patient in any other suitable fashion.

It should be understood that any feature(s) and/or operability described herein with respect to one particular retrieval bag (60, 160, 200, 300, 400, 500) may be incorporated into any other retrieval bag (60, 160, 200, 300, 400, 500) described herein. For instance, any of the retrieval bags (60, 160, 200, 300, 400, 500) described herein may comprise one or more fluid chambers, such as bladders (162, 164, 202, 204, 206) and/or fluid pockets (310, 410) to deploy, open, and/or seal retrieval bag (60, 160, 200, 300, 400, 500). Therefore, none of the teachings herein should be understood as being applicable to only one particular version or embodiment of retrieval bag (60, 160, 200, 300, 400, 500) described herein. Every teaching herein is contemplated as being interchangeable among versions and embodiments, such that every teaching herein may be applied to any retrieval bag (60, 160, 200, 300, 400, 500) described herein. Various ways in which the teachings herein may be interchanged among various versions and embodiments will be apparent to those of ordinary skill in the art in view of the teachings herein.

As noted above, the various versions of retrieval device (10, 110) described herein, including but not limited to the various versions of retrieval bag (60, 160, 200, 300, 400, 500) described herein, may be used in a conventional endoscopic procedure that includes the insertion of the introducer tube (20, 120) or other component through a small opening, e.g., an incision, natural orifice, or trocar access port, etc. Of course, retrieval device (10, 110) may be used in conjunction with any other suitable surgical or medical procedure, such as endoscopic/laparoscopic procedures, open surgical procedures, or robotic-assisted surgery, etc. Still other various settings and combinations in which a retrieval device (10, 110) or retrieval bag (60, 160, 200, 300, 400, 500) may be used will be apparent to those of ordinary skill in the art in view of the teachings herein.

While several specimen retrieval instruments, and components thereof, have been discussed in detail above, it should be understood that the components, features, configurations, and methods of using the specimen retrieval instruments discussed are not limited to the contexts provided above. In particular, components, features, configurations, and methods of use described in the context of one of the specimen retrieval instruments may be incorporated into any of the other specimen retrieval instruments. One merely exemplary additional feature that may be provided in any of the specimen retrieval instruments described herein includes retrieval bags having various sizes and geometries. For example, some specimen retrieval instruments may be designed with small, medium, or large retrieval bags. Also for example, some tissue retrieval instruments may use retrieval bags having pleats and/or gussets that allow for expansion when holding larger specimens. It should also be understood that any of the specimen retrieval instruments and tissue retrieval bags described herein may be capable of receiving tissue specimens and removing tissue specimens from a patient without such tissue specimens needing to be morcellated or otherwise reduced in size before being received and removed by the specimen retrieval instrument and bag. Still other additional and alternative suitable components, features, configurations, and methods of using the specimen retrieval instruments will be apparent to those of ordinary skill in the art in view of the teachings herein.

Other features and modifications that will be appreciated based on the teachings herein involve methods of attaching a retrieval bag to any of the various arms and loops or other components of a specimen retrieval instrument described above. For example, retrieval bags may be configured with one or more sleeves, slots, pockets, loops, slits, etc., for receiving any of the various arms and loops described above. In other versions, retrieval bags may be connected to any of the various arms, loops, or other components using suitable mechanical or chemical means. It will further be appreciated that in some versions the retrieval bag may be detachable from the other components of the specimen retrieval instrument, while in some other versions the retrieval bag may be inseparable from the specimen retrieval instrument. Still other additional and alternative suitable components, features, configurations, and methods of attaching retrieval bags with the other components of a specimen retrieval instrument will be apparent to those of ordinary skill in the art in view of the teachings herein.

It should also be understood that the components, features, configurations, and methods of use described in the context of one of the retrieval bags may be incorporated into any of the other retrieval bags. One merely exemplary additional feature that may be provided in any of the retrieval bags described herein is one or more weld lines. Such weld lines may be intermittent or continuous along the length of the bag. Such weld lines, offering alternating areas of stiffness along the surface of the bag, may enhance the closure of a bag due to the tendency of areas of lesser stiffness to buckle, deform, or fold. In this way, a retrieval bag may be forced or encouraged to buckle or fold in a desired manner as the bag is closed. Still other additional and alternative suitable components, features, configurations, and methods of using the above-described retrieval devices will be apparent to those of ordinary skill in the art in view of the teachings herein.

While the tissue retrieval instruments of the above-described examples are actuated manually by advancing a thumb ring distally relative to finger rings, it should be understood that any of the tissue retrieval instruments described herein may instead be actuated in any other suitable fashion. By way of example only, a tissue retrieval instrument may instead be actuated electromechanically (e.g., using one or more electrical motors, solenoids, etc.), pneumatically, and/or hydraulically. Various suitable ways in which such alternative forms of actuation may be provided in a tissue retrieval instrument will be apparent to those of ordinary skill in the art in view of the teachings herein. Similarly, various other suitable ways in which a tissue retrieval instrument may be actuated will be apparent to those of ordinary skill in the art in view of the teachings herein.

It should be understood that any of the retrieval bags described herein may have various types of construction. By way of example only, any of the retrieval bags described herein may be constructed from at least one layer of an elastomeric or polymeric material such as but not limited to polyurethane, polyethylene, polypropelene, polyester (Duralar), Poly-isoprene, silicone, vinyl, or a polytetrafluroethylene (Teflon®). For example, any retrieval bag described herein may comprise a single layer of elastomeric or polymeric material. Alternatively, any retrieval bag described herein may be formed of two or more layers of material. For instance, two or more layers of a retrieval bag wall may be aligned and joined together by adhesives, heat welding, heat staking, RF welding, ultrasonically welding, or other suitable method of attachment. Any retrieval bag described herein may also be cut at an angle to provide a taper or special shapes suitable for specific organs of body (e.g., tissue shapes, etc.), which may facilitate removal of the retrieval bag from a patient. Furthermore, any retrieval bag described herein may incorporate flexible metal meshes, thermoformed plastic meshes, fabrics, or aramid fibers such as Kevlar® for reinforcement. Still other suitable materials that may be used to form retrieval bags as described herein, including combinations of materials, will be apparent to those of ordinary skill in the art in view of the teachings herein. Similarly, various other suitable compositions of the walls of the retrieval bags described herein, including but not limited to various structures, components, and features that may be incorporated into the walls of the retrieval bags described herein, will be apparent to those of ordinary skill in the art in view of the teachings herein.

In any of the above described tissue retrieval instruments, the tissue retrieval bag may include a fold-over flap (not shown) for closing the bag. For instance, such a fold-over flap may be used instead of (or in addition to) using a string to effect closure of the bag. Such a fold-over flap may include an adhesive (e.g., pressure sensitive adhesive, etc.) that substantially keeps the flap in a closed position after the flap has been moved to a closed position. A peel-away strip or similar feature may be used to cover such an adhesive before the flap is closed. A conventional grasping instrument or other type of device may be used to peel the peel-away strip and/or close the flap over the mouth of the bag while the bag is still inside the patient. In some other variations, a tissue retrieval bag may be formed at least in part of a material that provides significant static adhesion or other type of adhesion to itself. For instance, the interior surfaces of the tissue retrieval bag may be configured to adhere to each other and/or to adhere to tissue/objects placed in the bag, to reduce the likelihood of tissue/objects in the bag falling out of the bag. In some such versions, a closure string is omitted. Other suitable variations of a tissue retrieval bag will be apparent to those of ordinary skill in the art in view of the teachings herein.

Versions of the present invention have application in conventional endoscopic and open surgical instrumentation as well as application in robotic-assisted surgery.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A surgical instrument for removal of material from a patient, the surgical instrument comprising:
   a. a handle assembly;
   b. an introducer tube, wherein the introducer tube is sized for insertion through a trocar, wherein the introducer tube comprises a proximal end and a distal end, wherein the proximal end of the introducer tube is in communication with the handle assembly, wherein the introducer tube includes an aperture proximally spaced from the distal end of the introducer tube, wherein the introducer tube further includes one or more indentations formed at the distal end of the introducer tube;
   c. a retrieval bag, wherein the retrieval bag is positionable at the distal end of the introducer tube, wherein the retrieval bag has an inflatable portion, wherein the retrieval bag is configured to receive a tissue specimen;
   d. an actuator rod slidably disposed in the introducer tube; and
   e. a distal plug at the distal end of the actuator rod, wherein the distal plug includes a resilient tab, wherein the actuator rod is translatable from a proximal position to a distal position to push the distal plug distally and thereby deploy the retrieval bag from the introducer tube;
   wherein the aperture of the introducer tube is configured to engage and receive the resilient tab of the distal plug to restrict proximal movement of the distal plug when the actuator rod reaches the distal position
   wherein the one or more indentations of the introducer tube are configured to restrict distal movement of the distal plug when the actuator rod reaches the distal position.

2. The surgical instrument of claim 1, wherein the retrieval bag defines an opening having a perimeter, wherein the inflatable portion comprises an annular bladder positioned about the perimeter of the opening.

3. The surgical instrument of claim 2, wherein the retrieval bag is formed by at least two adjacent layers of material, wherein the annular bladder is formed by portions of the two adjacent layers of material being separable from each other along a first region, wherein the two adjacent layers of material are inseparable from each other along a second region.

4. The surgical instrument of claim 1, wherein the retrieval bag has a length extending transversely relative to the introducer tube, wherein the inflatable portion comprises at least one rib bladder extending along at least part of the length of the retrieval bag.

5. The surgical instrument of claim 4, wherein the retrieval bag is formed of a material resiliently to assume a contracted configuration, such that the retrieval bag has a substantially flat and closed configuration when the at least one rib bladder is un-inflated, wherein the at least one rib bladder is configured to expand the retrieval bag to a substantially elongate and open configuration when the at least one rib bladder is inflated.

6. The surgical instrument of claim 1, wherein the retrieval bag is formed by at least two adjacent layers of material, wherein the retrieval bag has a length, wherein the two adjacent layers of material extend along the length of the retrieval bag, wherein the two adjacent layers of material are substantially loose relative to each other, such that the two adjacent layers of material define the inflatable portion between the two adjacent layers of material.

7. The surgical instrument of claim 6, wherein the inflatable portion is configured to substantially enclose a tissue specimen within the retrieval bag upon inflation of the inflatable portion.

8. The surgical instrument of claim 1, further comprising an inflator in fluid communication with the retrieval bag, wherein the inflator is operable to communicate a fluid medium to the inflatable portion of the retrieval bag to inflate the inflatable portion of the retrieval bag.

9. The surgical instrument of claim 8, wherein the inflator is secured to the handle assembly.

10. The surgical instrument of claim 8, wherein the inflator comprises a rod extending through the handle assembly, wherein the rod is translatable within the introducer tube to communicate a fluid medium to the inflatable portion of the retrieval bag to inflate the inflatable portion of the retrieval bag.

11. The surgical instrument of claim 8, further comprising a fluid conduit, wherein the fluid conduit is configured to couple the inflatable portion with the inflator.

12. The surgical instrument of claim 1, wherein the retrieval bag is positioned within the introducer tube when the actuator rod is in the proximal position, wherein the retrieval bag extends from the distal end of the introducer tube when the actuator rod is in the distal position.

13. The surgical instrument of claim 1, further comprising a resilient frame, wherein the resilient frame is positionable at the distal end of the introducer tube, wherein the retrieval bag is secured to the resilient frame.

14. The surgical instrument of claim 13, wherein the resilient frame extends distally from the actuator rod.

15. The surgical instrument of claim 14, wherein the resilient frame is collapsibly positioned within the introducer tube when the actuator rod is in the proximal position, wherein the resilient frame extends from the distal end of the introducer tube when the actuator rod is in the distal position.

16. The surgical instrument of claim 13, wherein the resilient frame comprises a resilient hoop member.

17. The surgical instrument of claim of claim 1, wherein the retrieval bag is sensitive to an environmental condition such that exposure of the retrieval bag to the environmental condition causes the retrieval bag to expand.

18. The surgical instrument of claim 1, wherein the handle assembly comprises a pair of finger grips.

19. The surgical instrument of claim 18, wherein the actuator rod comprises a thumb ring disposed at the proximal end of the actuator rod, wherein the thumb ring is disposed proximal to the pair of finger grips of the handle assembly.

* * * * *